(12) United States Patent
Suzuki

(10) Patent No.: US 6,417,512 B1
(45) Date of Patent: Jul. 9, 2002

(54) SAMPLE DISTORTION REMOVING METHOD IN THIN PIECE FORMING

(75) Inventor: Hidekazu Suzuki, Chiba (JP)

(73) Assignee: Seiko Instruments, Inc., Chiba (JP)

( * ) Notice: Subject to any disclaimer, the term of this patent is extended or adjusted under 35 U.S.C. 154(b) by 0 days.

(21) Appl. No.: 09/356,014

(22) Filed: Jul. 16, 1999

(30) Foreign Application Priority Data

Jul. 16, 1998 (JP) .......................................... 10-202299

(51) Int. Cl.⁷ ................................................ H01J 37/26
(52) U.S. Cl. ................... 250/307; 250/309; 250/492.21
(58) Field of Search ................................ 250/309, 311, 250/492.21, 492.3, 307, 310

(56) References Cited

U.S. PATENT DOCUMENTS

| | | | | |
|---|---|---|---|---|
| 4,933,565 A | * | 6/1990 | Yamaguchi et al. | 250/492.2 |
| 5,093,572 A | * | 3/1992 | Hosono | 250/310 |
| 5,113,072 A | * | 5/1992 | Yamaguchi et al. | 250/309 |
| 5,525,806 A | * | 6/1996 | Iwasaki et al. | 250/492.21 |
| 5,770,861 A | * | 6/1998 | Hirose et al. | 250/310 |
| 5,986,264 A | * | 11/1999 | Grunewald | 250/310 |
| 6,218,663 B1 | * | 4/2001 | Nisch et al. | 250/309 |

OTHER PUBLICATIONS

Japanese Patent Abstract, No. 04–076437.
Japanese Patent Abstract, Catalog No. AP 901110–02.

* cited by examiner

*Primary Examiner*—Kiet T. Nguyen
(74) *Attorney, Agent, or Firm*—Pillsbury Winthrop LLP

(57) ABSTRACT

A method of removing warp distortions of a thin-piece sample for use in an electron microscope during the formation of the sample. The sample is cut to form a fissure in a stress concentration portion of the sample using an ion beam until the warp distortions disappear. The stress concentration often occurs at a device region having material anisotropy in the sample, and the distortion is removed by forming a fissure in a depth direction of the sample.

10 Claims, 3 Drawing Sheets

SAMPLE DISTORTION REMOVING METHOD IN THIN PIECE FORMING

BACKGROUND OF THE INVENTION

The present invention relates to a method of eliminating warp distortions occurring in the course of forming thin-piece samples for use in transmission electron microscopes (TEM), etc., using a focused ion beam (FIB).

Section TEM samples are required to be formed so that the desired point of observation is at a thickness through which an electron beam can be transmitted. Conventionally, it has been well known that an ion beam may be used to form a test/examination sample into a desired shape. Forming a sample for use in a transmission electron microscope (TEM) is performed by cutting the sample, using a focused ion beam, to a proper thickness so that electrons can transmit through the sample. This sample forming method is disclosed in the reference entitled, "Section TEM Sample Forming Method Using a Focused Ion Beam", 37th Applied Physical Academy, March 1990. Also, Japanese Patent Application No. 192641/1990 (JP-A-4-76437), filed by the present applicant, is also related to this technology. When a sample is machine-polished down to approximately several 10 $\mu$m, it is further cut at opposite surfaces of an observational point by ion beam etching so as to leave a thin wall of less than 1 $\mu$m, which makes it more convenient to confirm and observe a forming position, forming shape, section, etc. The prior application discloses an invention where a scanning electron microscope irradiating an electron beam is arranged so as to form a sample while monitoring a forming portion of the sample. Furthermore, disclosure is also made of the technology where the sample surface is locally formed with a film so as to prevent any damage due to the ion beam, and the inclination angle of a forming surface resulting from a convergent angle of the ion beam is compensated for by using an inclination setting in a table holding the sample in order to produce evenness in the sample thickness.

A summary of the basic technology of a focused ion beam forming apparatus for the present invention will be explained referring to an embodiment of the prior application shown in FIG. 3.

When a sample 4 to be formed is placed on a stage 5, the sample chamber is placed in a vacuum state by a vacuum apparatus (not shown). The sample stage 5 is set to a desired positional angle by a drive mechanism (not shown). The drive mechanism, in general, is capable of: (1) displacement in the X, Y and Z directions, (2) ion beam axis rotation, and (3) adjustment in angle relative to an ion beam axis. When a forming region is determined, a region of the sample having an end portion of a thin wall is exposed to a chemical vapor deposition (CVD) gas from the gas gun 9 in order to prevent damage to the portion by the ion beam, and a metal protection film is formed. Next, the forming region is irradiated by an ion beam and cut by sputtering. In this case, the relative displacement of the ion beam 2 and the sample 4 is made by scanning the ion beam with the deflection means of the electrostatic optical system 3, without using a drive device, because the forming requires extreme precision on the order of microns. Initially, the ion beam current is adjusted to increase the sputter rate in order to shorten the process time, thereby performing rough forming. Finally, the ion current is decreased in the area of the sample forming region, thereby performing precision forming. The feature of this apparatus lies in a structure where an electron beam can be irradiated to a sample for sample surface observation in a direction different than that of the ion beam. Because of this arrangement, an electron beam 7 may be solely used for scanning a sample that would have been damaged by an ion beam. The secondary charged particles (electrons) 11 are then detected by the secondary charged particle detector 10. Thus, observations may be made at the same time the samples are formed without taking the samples out of the apparatus. Also, because scanning electron microscope (SEM) images and scanning ion microscope (SIM) images are different due to the different kinds of secondary charged particles 11 emitted from the sample, images having different resolutions may be obtained. Accordingly, both images can be compared side-by-side on a display 13.

FIGS. 2A to 2D refer to the forming of a sample for use in a transmission electron microscope (TEM). A holding piece (not shown) is fixed with a sample block 4 that is mechanically cut out and is placed on a sample table (stage) 5 of the focused ion beam apparatus through a holder (not shown), and an ion beam 2 is irradiated to form the sample (see also FIG. 3). The specific procedure is as follows. In the first step, as shown in FIG. 2A, a sample 4 is a sectionally convex-formed block formed by mechanical cutting, and the sample is placed on the sample stage 5 (see FIG. 3). Next, a forming frame of the sample is determined, and, in order to prevent damage by the irradiating ion beam to the end portion being formed into a thin wall, a CVD gas (e.g., phenanthrene $C_{14}H_{10}$) is applied to that portion, thereby forming a protective coating layer 41 (as shown in FIG. 2B). In the next step, an ion beam 2 is irradiated and the sample block is cut at opposite surfaces by sputtering. Thus, a thin wall 42 of a sample becomes formed as shown in FIG. 2C. This sample for use in a transmission electron microscope has no differences in the shape of the opposite surfaces, and the sample is required to be of a thickness where an incoming electron beam 7 to the thin wall from a perpendicular direction can transmit through the thin wall (being 0.5 $\mu$m or less), as shown in FIG. 2D.

When the reduction of thickness of the sample is proceeded by ion beam forming, there is a chance that the thin-walled portion of the sample will become distorted and warped, as if a celluloid board is bent by pressing at opposite ends. If the sample becomes distorted or warped, and even if an ion beam is linearly scanned, it becomes impossible to perform planar forming with an even thickness because of the distortion. FIG. 1A is a top view of a sample having a thin wall where warp distortion occurred. Conventionally, when distortion occurs, the sample block had to be replaced and the forming operation had to be performed again from the beginning. However, where the samples are composed of the same materials and the structures are the same, if distortion occurs once during forming, then chances are that distortions will be unavoidable in forming samples composed of similar materials and having similar structures.

Another disadvantage is that if the sample forming is suspended at a stage of thickness before the deformation occurs, electron transmissibility may be too low, or non-coincident portions may be left in the opposite surfaces, which becomes unsatisfactory for use as a TEM sample. Referring to FIG. 1C, if pillars 43 are left in the midway of an observational region and the thin wall 42 width is narrow, the phenomenon of warp distortion will not occur. However, in such a case, the observational region is limited, but more importantly, this type of forming requires much time and labor, and therefore this type of forming is not preferred.

The present invention is aimed at providing a forming method capable of easily and more efficiently preparing a thin-piece sample for use in a transmission electron microscope by eliminating warp distortion of a sample during the formation process of thin-piece sample.

SUMMARY OF THE INVENTION

The present invention is directed to a method of removing warp distortions of a thin-piece sample for use in an electron microscope during the formation of the sample. The sample is cut to form a fissure in a stress concentration portion of the sample using an ion beam until the warp distortions disappear. The stress concentration often occurs at a device region having material anisotropy in the sample, and the distortion is removed by forming a fissure in the depth direction of the sample.

DETAILED DESCRIPTION OF THE INVENTION

Figure 1A:
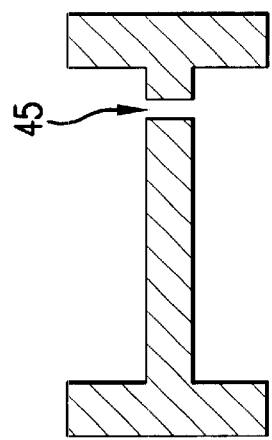
FIG. 1A is a top view from an ion beam source of a warp distortion of a sample in the vicinity of a thin-wall end portion.
Figure 1B:
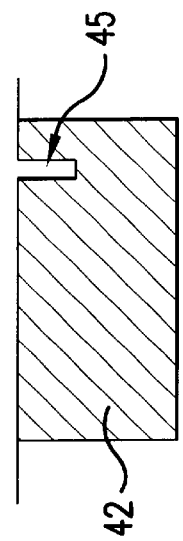
FIG. 1B is a top view from an ion beam source of an end portion where distortion is eliminated by forming a fissure from the end portion according to an embodiment of the present invention.
Figure 1C:
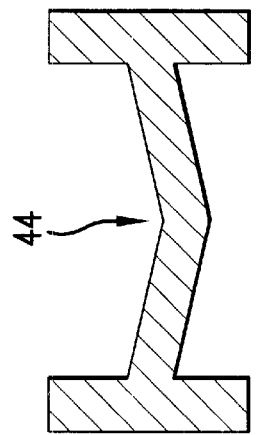
FIG. 1C is a top view of the vicinity of a thin-wall end portion having pillars in the midway of the thin wall.
Figure 1D:
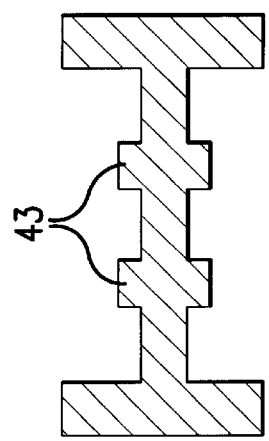
FIG. 1D is a side view of a thin-wall end portion according to FIG. 1B where distortion is eliminated by forming a fissure according to an embodiment of the present invention.
Figure 2A:
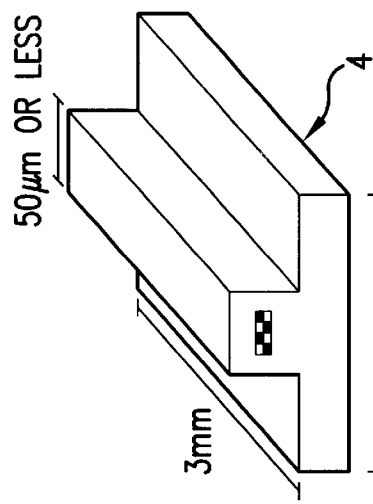
FIG. 2A is a perspective view of a sample block formed by mechanical cutting.
Figure 2B:
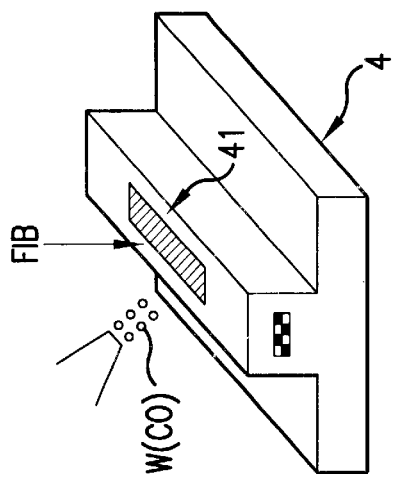
FIG. 2B is a perspective view showing a metal protection film formed at the thin-wall end portion using a gas gun and then irradiated by an ion beam.
Figure 2C:
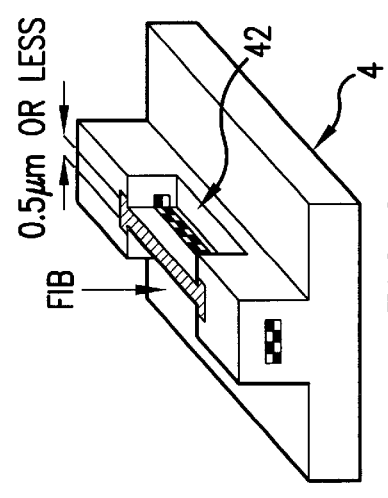
FIG. 2C is a perspective view of a sample formed into a thin piece by an ion beam.
Figure 2D:
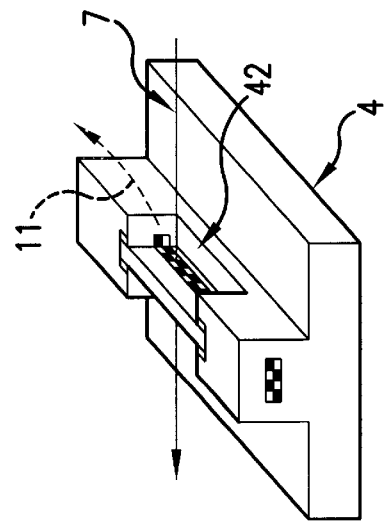
FIG. 2D is a perspective view showing a positional relationship between a created TEM sample and a transmission electron beam.
Figure 3:
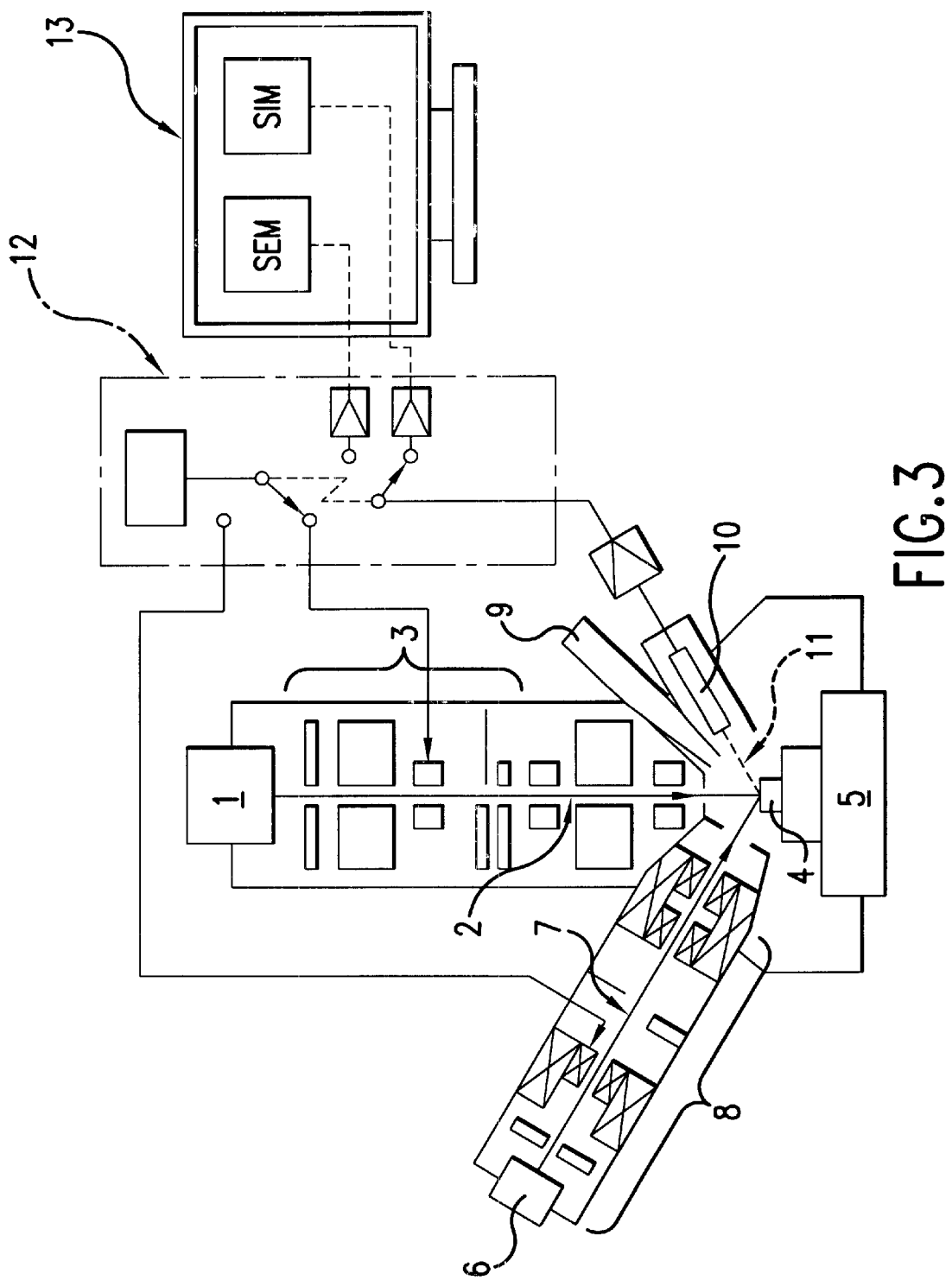
FIG. 3 is a schematic view showing an example of an ion beam forming apparatus.

The thin piece forming of a transmission electron microscope sample by an ion beam requires that there are no differences in the shape of the opposite surfaces, and that the sample is preferably formed to a thickness where an electron beam 7 emitted in a perpendicular direction to the thin wall 42 can transmit through the thin wall (being 0.5 $\mu$m or less), as shown in FIG. 2D. If there is a difference between the opposite surface shapes, it would be impossible to obtain an accurate transmission microscopic image, even if the electrons can transmit through the sample thin wall 42. Accordingly, during formation of the sample, the opposite surfaces are constantly observed. The observation in this case may be conducted by using a scanning electron microscope (SEM) where an electron beam 7 is irradiated in a direction different from the ion beam. If a warp distortion occurs on the sample as shown in FIG. 1A, it can be detected during this observation. Although the state of the warped distortion 44 of the thin wall 42 is a distortion on an end side as shown in FIG. 1A, there is generally no distortion on a block substrate side due to its continuation to the substrate. If a warp distortion 44 is found, ion beam forming is suspended and an ion beam is irradiated from the top of the sample to form a fissure 45. This operation is monitored by a SEM image (although a SIM image may be used depending on the specific circumstances). The ion beam irradiation is stopped when the warp distortion disappears. Because the apparatus provided with the scanning electron microscope irradiates an ion beam 2 and an electron beam 7 to the sample in different directions, any warp distortions that appear during the sample formation may be observed using a SEM image produced by the electron microscope. The point where stress concentration occurs, in most cases, is in a conductor member portion in a relatively shallow device layer. If this portion is cut by a fissure 45, stresses are released and the distorted thin wall 42 smoothly restores to a flat wall surface 42. Referring to FIGS. 1B and 1D, the fissure 45 is not necessarily formed deeply, and in most cases, if the fissure 45 is formed in the upper layered device portion, warp distortion is eliminated. In this state, the thin-piece forming process is allowed to proceed and the ion beam forming is continued to perform thickness reduction to a desired thickness, thus fabricating the TEM sample.

In the forming method of an embodiment of the present invention, when a warp distortion occurs in a thin wall portion of a sample to be formed during the course of the thin-piece forming process, a fissure 45 is formed from an end portion side of the thin wall. If the stress concentration portion is cut, stresses are released and the warp distortion is eliminated to restore a flat thin wall, thereby enabling continuation of the thin-piece forming process with the ion beam. Accordingly, warp distortion is easily eliminated, and a TEM sample can be formed efficiently without wasting time and extra materials.

Also, when this forming process is practiced using an ion beam forming apparatus provided with a scanning electron microscope, it is possible to observe a SEM image while performing the thin-piece forming without having to remove the sample from the apparatus in the middle of the forming process and confirming the shape with a separate SEM, and thereafter again continuing the forming process. A warp distortion on the thin-wall sample can be swiftly detected by the imaging of the SEM. By creating a fissure during sample formation, the entire forming process can be made within one apparatus. Moreover, because these operations can all be performed in a single apparatus, it is no longer necessary to repeat the operations of sample insertion and removal, positioning, and vacuum evacuation. Therefore, it is possible to carry out the entire operation with extreme efficiency and ease.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes that come within the meaning and range of equivalency of the claims are therefore intended to be embraced therein.

What is claimed is:

1. A method of forming a thin-piece sample for use in a transmission electron microscope, comprising:
   irradiating an ion beam to form the thin-piece sample; and
   irradiating an ion beam to form a fissure in a stress concentration portion of the sample until a warp distortion, which occurs during formation of the thin-piece sample, disappears.

2. The method according to claim 1, wherein the fissure is formed in a device layer portion of the sample from a thin-wall end portion in a depth direction.

3. The method according to claim 2, further comprising the step of:

using a scanning electron microscope to observe occurrences of warp distortions during formation of the sample by the ion beam.

4. The method according to claim 1, further comprising the step of:

using a scanning electron microscope to observe occurrences of warp distortions during formation of the sample by the ion beam.

5. A method of forming a thin-piece sample for use in a transmission electron microscope, comprising:

irradiating an ion beam to form the thin-piece sample;

forming, with the ion beam, a fissure in a stress concentration portion of the thin-piece sample if a warp distortion, which occurs during formation of the thin-piece sample, begins to appear;

continuing to form the fissure until the warp distortion disappears; and resuming irradiation of the ion beam to form the thin-piece sample.

6. The method according to claim 5, wherein the fissure is formed in a device layer portion of the sample from a thin-wall end portion in a depth direction.

7. The method according to claim 6, further comprising the step of:

using a scanning electron microscope to observe occurrences of warp distortions during formation of a sample by the ion beam.

8. The method according to claim 5, further comprising the step of:

using a scanning electron microscope to observe occurrences of warp distortions during formation of the sample by the ion beam.

9. A method of forming a thin-piece sample without warp distortions using a device having a combination of a scanning electron microscope and an ion beam forming apparatus, wherein the thin-piece sample is for use in a transmission electron microscope, comprising:

irradiating an ion beam from the ion beam forming apparatus to form the thin-piece sample;

using the scanning electron microscope to observe occurrences of a warp distortion during formation of the thin-piece sample by the ion beam;

forming, with the ion beam, a fissure in a stress concentration portion of the thin-piece sample if the warp distortion, which occurs during formation of the thin-piece sample, begins to appear;

continuing to form the fissure until the warp distortion disappears; and resuming irradiation of the ion beam to form the thin-piece sample.

10. The method according to claim 9, wherein the fissure is formed in a device layer portion of the sample from a thin-wall end portion in a depth direction.

* * * * *